(12) United States Patent
Dilmanian et al.

(10) Patent No.: US 8,269,198 B2
(45) Date of Patent: Sep. 18, 2012

(54) HEAVY ION THERAPY WITH MICROBEAMS

(75) Inventors: F. Avraham Dilmanian, Yaphank, NY (US); Allen G. Meek, Mount Sinai, NY (US)

(73) Assignee: F. Avraham Dilmanian, Yaphank, NY (US)

( * ) Notice: Subject to any disclaimer, the term of this patent is extended or adjusted under 35 U.S.C. 154(b) by 328 days.

(21) Appl. No.: 12/692,216

(22) Filed: Jan. 22, 2010

(65) Prior Publication Data

US 2010/0187446 A1 Jul. 29, 2010

Related U.S. Application Data

(60) Provisional application No. 61/146,681, filed on Jan. 23, 2009.

(51) Int. Cl.
*A61N 5/10* (2006.01)
(52) U.S. Cl. .................................. 250/492.3; 250/505.1
(58) Field of Classification Search ................ 250/492.3, 250/505.1
See application file for complete search history.

(56) References Cited

U.S. PATENT DOCUMENTS

| | | | |
|---|---|---|---|
| 4,672,212 A * | 6/1987 | Brahme | 250/505.1 |
| 5,339,347 A | 8/1994 | Slatkin et al. | |
| 5,668,371 A * | 9/1997 | Deasy et al. | 850/1 |
| 7,158,607 B2 | 1/2007 | Dilmanian et al. | |
| 7,194,063 B2 * | 3/2007 | Dilmanian et al. | 378/65 |
| 7,834,336 B2 * | 11/2010 | Boeh et al. | 250/505.1 |
| 7,982,200 B2 * | 7/2011 | Keppel et al. | 250/505.1 |
| 8,076,657 B2 * | 12/2011 | Mackie et al. | 250/492.3 |

* cited by examiner

Primary Examiner — Jack Berman
(74) Attorney, Agent, or Firm — Hoffmann & Baron, LLP

(57) ABSTRACT

A method for delivering therapeutic heavy ion radiation to a subject, wherein a therapeutic dose of heavy ions is delivered substantially only to a target volume within the subject by generating a broad field of radiation effect substantially only within the target volume, and wherein the broad field of radiation effect is not generated in non-targeted tissue. The method includes the step of irradiating the target volume with at least two arrays of heavy ion microbeams, wherein the at least two arrays each have at least two parallel, spatially distinct heavy ion microbeams. The two arrays of microbeams are interleaved substantially only within the target volume to form a substantially continuous broad beam of radiation substantially only within the target volume.

16 Claims, 5 Drawing Sheets

HEAVY ION THERAPY WITH MICROBEAMS

CROSS-REFERENCE TO RELATED APPLICATIONS

This application claims the benefit of U.S. Provisional Application No. 61/146,681, filed on Jan. 23, 2009, the specification of which is incorporated by reference herein in its entirety for all purposes.

BACKGROUND OF THE INVENTION

The present invention relates generally to methods for performing microbeam therapy on a subject for treatment of tumors, neurological targets and of other diseases, and more particularly to methods of delivering therapeutic microbeam arrays of protons and heavy ions to produce a broad beam, i.e., solid beam effect only within a target volume thus increasing the therapeutic effect of the microbeam radiation therapy method.

Cancer continues to be one of the foremost health problems. Conventional treatments such as surgery, chemotherapy and radiation therapy have exhibited favorable results in many cases, while failing to be completely satisfactory and effective in all instances. For example, conventional radiation therapy has serious limitations due to radiation damage to normal tissues. Although stereotactic radiosurgery has improved the outcomes, highly radiosensitive structures located in the vicinity of the target remain a limiting factor. It is well known to those skilled in the art that the threshold dose, or maximum tolerable dose before neurological and other complications of radiotherapy arise, increases as irradiated volumes of tissue are made smaller. Such observations eventually led to the development of grid radiotherapy using grids or sieves for spatial fractionation of the X-ray exposure field at the body's surface, and also to the development of stereotactic radiosurgery.

Recently, an alternative form of radiation therapy, known as microbeam radiation therapy (MRT), has been investigated in laboratory animals to treat tumors such as those for which the conventional methods have limited effectiveness or are associated with a high risk factor. The concept of MRT was introduced in U.S. Pat. No. 5,339,347 to Slatkin et al. MRT differs from conventional radiation therapy by employing arrays of parallel planes of x-rays, which are at least one order of magnitude smaller in thickness (or diameter if parallel cylindrical beams are used rather than planar beams) than the smallest radiation beams in current conventional clinical use. These very thin microbeams, which are also called microplanar beams, can be generated using the high intensity x-ray beams that are currently generated only at synchrotron electron storage rings.

The tissue-sparing effect of microbeams for beam thicknesses between 0.02 mm and 0.7 mm has been established in a large variety of tissue types, including the brain and spinal cord in very young and adult laboratory animals. This tissue-sparing phenomenon has been attributed to two separate effects. According to the first effect, called the "dose-volume tissue-repair effect," tissues can tolerate larger doses when the irradiated volume is made smaller. According to the second effect, called "microscopic prompt tissue repair effect," when the beam thickness is a small fraction of a millimeter, several biological tissue repair mechanisms become effective promptly, i.e., within hours or days, and repair the damage to the tissue.

In a new development in MRT, two arrays of planar x-ray microbeams aimed at the target from 90-degreee angles were "interlaced" (or "interleaved") with each other to produce an unsegmented radiation field at the target. This concept is the subject of U.S. Pat. Nos. 7,158,607 and 7,194,063 to Dilmanian, the specifications of which are incorporated herein by reference. In order to obtain an unsegmented, i.e., solid radiation field at the target, the gaps between the microbeams are made equal or slightly smaller than the thickness of each microbeams, and one array is shifted with respect to the other in the direction perpendicular to the planes of the microbeams by half the value of the beam spacing on-center. Therefore, the target receives an unsegmented radiation field (i.e., broad or solid beam), which can be lethal at a single fraction of 30-90 Gy, while the normal tissues surrounding the target receive only segmented beams, which spare normal tissues at those doses.

There are four advantages interlaced x-ray microbeams have over the conventional, unsegmented beams (called broad beams) currently used in clinical radiation therapy. First, interlaced microbeams spare the normal tissues surrounding the tumor because they are exposed to single arrays of microbeams only, which is tissue sparing. Second, because the microbeams are produced by synchrotron sources, which produce highly parallel beams, and because their beam energy is much smaller than those used in conventional radiation therapy, the dose falls very sharply at the edge of the target volume. This allows the treatment of very small tumors or neurological targets without unnecessarily exposing much of the surrounding normal tissues. Third, the radiation is administered in a single exposure (called single dose-fraction) instead of up to 40 daily dose fractions used in conventional radiation therapy. Finally, in the treatment of the tumors in the brain and the spinal cord, because of the sparing effect of the microbeams in the surrounding normal tissues, the treatment can be repeated if the tumor re-grows or if later another tumor develops in the brain or in the vicinity of the first tumor in the spinal cord.

The interlaced microbeam radiation methods disclosed in the '607 and '063 Dilmanian patents use arrays of parallel planar beams, each 0.3 to 0.7 mm in thickness in which the beam spacing on-center is twice the beam thickness (and therefore the gaps between the beams is equal to the beam thickness). In this method the target is aimed with two such arrays from orthogonal angles in a configuration in which the microplanar beams in the two arrays are parallel to each other. One array is shifted with respect to the other in the direction of the vector perpendicular to the microplanar beams by a distance equal to the gap between the beams. As a result, the two arrays interlace at the target, producing a non-segmented radiation field at the target.

However, a problem with x-ray microbeam delivery systems involves an important concept known as the "valley dose." The term "valley dose" refers to the radiation leakage between microbeams of x-rays caused mostly by x-ray scattering. This leakage or scattering of x-rays between the delivered beams can damage normal tissue not being targeted, or jeopardize the otherwise robust biological repair processes involved with microbeam irradiations of normal tissues. For the normal tissues surrounding the target to be spared from the radiation, the valley dose in the normal tissue should be adequately low to allow the supportive cells in charge of tissue repair to survive.

Protons and heavy ions, mostly carbon, are also being used in clinical radiation therapy with some success. They have two main advantages over x-rays in their implementation for radiation therapy. First, because of their Bragg-peak feature of dose distribution in tissues in which the dose is mostly deposited in the last few millimeters of the particles' trajectory, and consequently because of their lack of target exit dose, they produce tighter dose distributions around the target volume than x-rays. Second, heavy charged particles particularly heavy ions such as carbons have a much larger Radiobiological Effectiveness (RBE) than x-rays, a factor that is particularly important in treating hypoxic and other radio resistant tumors. In particular, the RBE of heavy ions can be as large as 4.0, while that of protons is commonly less than 1.3.

Although the results from proton therapy are generally better than those from the present x-ray and gamma-ray (as in gamma-knife) methods, the difference is modest except probably for treating pediatric brain tumors. Furthermore, conventional heavy ion therapy has limitations because of its potential to damage normal tissues around the target at the therapeutic doses.

While protons have some advantages over x-rays, there has heretofore been no attempt to implement proton therapy with microbeams because their beams widen excessively as they pass through the tissue, an effect called "angular straggling." For example, the width of a 1 mm proton beam can increase to about 2.5 mm when passing through 12 cm of tissue. However, the angular straggling effect of heavy ions is much smaller than that for protons because of the higher linear momentum of the heavy ions for the penetration to same tissue depth.

Accordingly, it would be desirable to combine the technologies of microbeam radiation therapy with heavy ion therapy to address some of the difficulties encountered in today's radiation therapy and radiosurgery. In particular, there is a need in the medical field for effective implementation of heavy ion therapy utilizing modern microbeam technologies. Further, there is a need for efficient devices for implementing interlaced heavy ion microbeams, which greatly enhance the possibility of delivery of therapeutic dose at a target while maintaining a safe dose to normal tissue.

SUMMARY OF THE INVENTION

The present invention, which addresses the needs of the prior art, relates to a system and more efficient methods of heavy ion radiation therapy which greatly enhance the delivery of therapeutic dose and therefore production of damage to target tissue, such as a tumor, while simultaneously reducing damage to normal tissue in the path of the irradiating beam. This effect is achieved by implementing a concept which was originally developed for the x-ray microbeam technology with heavy ion beams.

In particular, it has been surprisingly found that heavy ions can not only be used as microbeams, but their inherent beam broadening characteristics can be used with meritorious effects in different administration methods of microbeam radiation therapy. The present invention uses the technique of implementing interlaced x-ray microbeams, as described above, in a configuration for radiation therapy with heavy ions.

In a method according to the present invention, therapeutic heavy ion radiation is delivered to a subject, wherein a therapeutic dose of heavy ions is delivered substantially only to a target volume within the subject by generating a broad field of radiation effect substantially only within the target volume, and wherein the broad field of radiation effect is not generated in non-targeted tissue. The method includes the step of irradiating the target volume with at least two arrays of parallel heavy ion microbeams, wherein the at least two arrays each have at least two parallel, spatially distinct heavy ion microbeams. The two arrays of microbeams are interleaved substantially only within the target volume to form a substantially continuous broad beam of radiation substantially only within the target volume.

The parallel, spatially distinct heavy ion microbeams have a beam thickness, a beam width and a beam spacing. The arrays of heavy ion microbeams have parallel beam planes and a substantially constant inter-beam spacing between adjacent microbeams, wherein the inter-beam spacing in each of the at least two incident arrays are substantially equal to or greater than the beam thickness. The step of interleaving at the target of the at least two arrays of microbeams includes the steps of irradiating the target volume in a first direction with a first one of the at least two arrays of heavy ion microbeams, angularly displacing a second one of the at least two arrays from the first one of the at least two arrays by rotating one of the subject or the source generating the at least two arrays 90-degrees about an axis positioned through a center of the target volume, the axis being perpendicular to the parallel beam planes, translating the second one of the at least two arrays in a direction perpendicular to the parallel beam planes by a distance substantially equal to half the value of beam-spacing on-center and irradiating the target tissue in a second irradiation direction with the second of the at least two arrays.

The incident arrays of heavy ion microbeams are preferably produced by placing a multi-slit collimator in the path of the incident broad-beam heavy ions coming from the accelerator. The collimator, which has slits with the size of the individual incident microbeams, is made of heavy metals.

The interbeam spacing between adjacent heavy ion microbeams of each array is preferably determined to be greater than the incident beam thickness to accommodate beam broadening on the way to the target. The criterion is that at the proximal side of the target the interbeam spacing will be slightly smaller that the beam thickness so that the two interleaving arrays touch each other and slightly overlap at that point to produce a solid radiation field at the target.

The maximum beam energy in each array will be chosen so that the deepest Bragg peak will be the distal side of the target. The technique of Bragg-peak spreading, which involves stepwise decreasing the beam energy from its maximum to produce a uniform dose distribution along the depth of the target, is preferably used in the exposures from each direction.

Because the radiation given from each direction stops at the distal side of target, it can be administered from four directions instead of two. This goal is achieved by angularly displacing the two arrays by one hundred eighty (180) degrees and repeating the first two irradiations.

The heavy ion microbeams can also be laterally segmented along their beam width leaving gaps regularly spaced in a direction parallel with the plane of the beam, wherein heavy ions are not present in the gaps. Such lateral segmentation can be accomplished by a collimator made of a heavy metal. A collimator can also be used to shape the cross-sections of the microbeams of the arrays to match the cross-sectional shape of the target volume in the desired irradiation direction. The new segments will merge as the plane approaches the target volume.

The method of the present invention further preferably takes into account the inherent broadening of the heavy ion microbeams to select an inter-beam spacing of the arrays so that a path of heavy ions irradiating the target volume from the first direction only intersects a path of heavy ions irradiating the target volume from the second direction upon entering the target volume and wherein the thickness of the beams entering the target volume is less than 0.8 mm. The heavy ions are selected from the group consisting of heavy ions of He, Li, Be, B, C, O, F, Na, Ne, and Mg, depending on the depth of the target volume within the subject so that the thickness of the beams entering the target volume is less than 0.8 mm.

The method according to the present invention can further include the step of spreading the Bragg-peak of the heavy ions among the microbeams to produce a uniform dose distribution throughout the target volume. This step can be achieved by stepwise adjusting the energy and intensity of the heavy ions in each microbeam or successively interposing plastic filters of varying thickness in the path of a microbeam. This step can further include the step of selecting heavy ions based on the relative biological effectiveness (RBE) number of the ions.

Arrays or parallel planar heavy ion beams are preferably implemented in the planar-beam interlacing geometry. As described above, the main difference between the administration of protons and heavy ions in this context is that protons undergo much more straggling than heavy ions. Therefore, to accommodate the differences in the beam's angular straggling, arrays of parallel heavy ion beams are preferably implemented in a planar-beam interlaced microbeam geometry. This can be done because of the smaller amount of angular straggling in heavy ion beams, as compared to proton beams. As a result, the gaps between the heavy-ion microbeams narrow only moderately as the beams penetrate the tissues. This allows production of an unsegmented field at deep targets while exposing the normal tissues proximal to the target to spaced apart microbeam arrays only at beam thickness values still retaining the microbeams' tissue-sparing effect. Moreover, the normal tissues distal to the target do not get much dose because there are essentially no exit beams for heavy ions beyond its Bragg peak (i.e., the beam essentially stops at the Bragg peak). As a result, the beam can be used from four orthogonal directions, thus reducing the necessary entrance dose by two-fold. Finally, each planar microbeam can be further segmented along the length of the plane, thus leading to a larger tissue-sparing effect at the proximal side of the target. The new segments will merge as the plane approaches the target volume.

As a result, the present invention provides more efficient methods of radiation therapy by employing microbeams of heavy ions in a particular geometry. The preferred embodiments of the heavy ion microbeam radiation therapy systems and methods of the present invention, as well as other objects, features and advantages of this invention, will be apparent from the following detailed description, which is to be read in conjunction with the accompanying drawings. The scope of the invention will be pointed out in the claims.

DETAILED DESCRIPTION OF THE PREFERRED EMBODIMENTS

Figure 1:
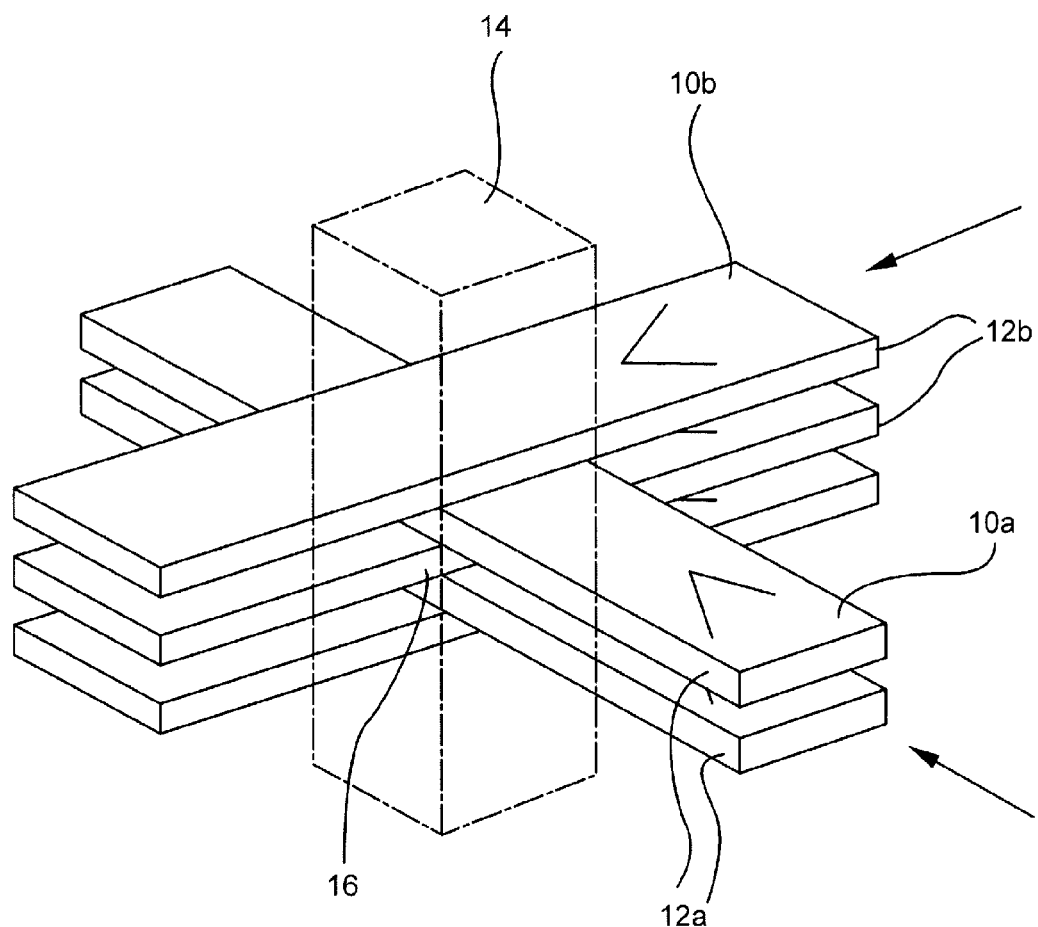
FIG. 1 is a perspective view of two interlacing arrays of planar x-ray microbeams of the prior art.

To best understand the present invention, a description of the prior art relating to techniques involving interlaced x-ray microbeams is first presented. FIG. 1 shows two arrays 10a, 10b of quasiparallel, planar x-ray microbeams 12a, 12b aimed at a target 14 from two orthogonal directions, according to the prior art. The beams 12a, 12b in each array are generally planar and are typically 0.4 mm thick and are spaced on-center at slightly less than twice that amount, i.e., at about 0.7 mm or less. The first microbeam array 10a is interleaved or interlaced with the second microbeam array 10b to form a substantially continuous three dimensional irradiation pattern at the target 14 where the microbeams in the two interleaving arrays touch and slightly overlap to produce a non-segmented radiation field. This produces a solid and nearly uniform pattern 16 of radiation only within the target tissue 14. It can also be seen that the x-ray beams are sharp, with no broadening.

The implementation of the interleaved or interlaced arrays 10a and 10b is achieved first by having the propagation planes of the rows of microbeams in the two arrays parallel to each other, and, second, by having one array shifted vertically (for the case where the microbeams are horizontal, as shown in FIG. 1), with respect to the other, or generally in the direction perpendicular to the microbeam rows by half the amount of beam spacing on-center.

The implementation of the two orthogonal arrays can be achieved by either rotating the subject or rotating the source. In both cases, the axis of rotation is generally positioned through the center of the target volume 14, and perpendicular to the microbeam planes. In this way, the beams 12a of the array 10a in the first irradiation direction remain substantially parallel to the beams 12b of the second array 10b after rotation.

In addition, the arrays 10a and 10b are non-intersecting arrays. In other words, the individual planar beams 12a of the first array 10a do not intersect the planar beams 12b of the second array 10b, but interlace or interleave with and touch each other at their edges to form a solid irradiation field 16 at the target. The slight overlap at the microbeams' edges produces a secure zone to assure that no gaps between the beams are produced inside the target because of small misalignment of the beams or small movement of the subject. For this reason, the value of the beam spacing on-center in each of the two arrays is slightly smaller than twice the value of the thickness of the beams.

Having discussed the prior art, the interlaced heavy ion microbeam technique of the present invention is now presented. First, the terms interlaced and interleaved are used interchangeably herein to refer to the concept, as described above with respect to x-rays, of providing an array of regularly spaced, parallel planar microbeams and directing the array from at least two different directions at a target to form a solid irradiation field at the target. Second, the major difference between the x-ray and the heavy-ion method is that the heavy ion microbeams broaden gradually as the beam penetrates the tissue, an effect called angular straggling.

Figure 2:
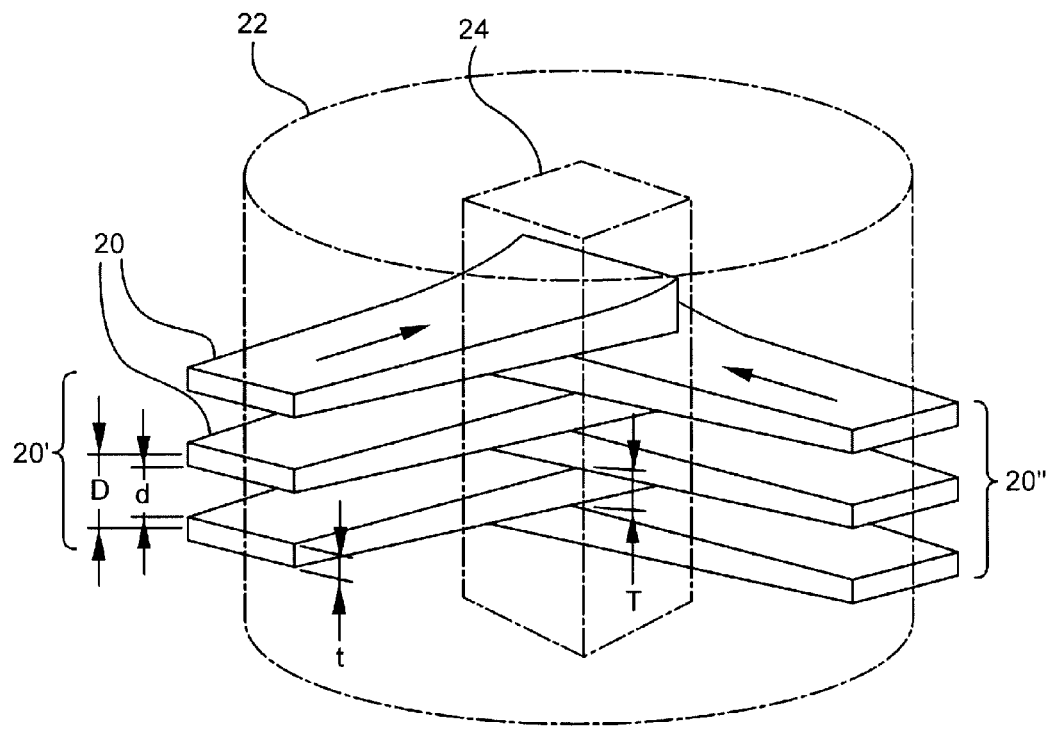
FIG. 2 is a perspective view of two interlacing arrays of planar heavy ion microbeams according to the present invention.

Specifically, as shown first in FIG. 2, in one embodiment of the present invention, a first array 20' of quasiparallel, planar heavy ion microbeams 20 is aimed at a target 22 from a first direction. The heavy ion beams 20 in the array are generally planar and are spaced a distance D from each other. A second array 20" of heavy ion beams 20 is aimed at the target 22 from a second direction different than the first direction of the first array. In a preferred embodiment, the first and second directions are generally perpendicular.

The first heavy ion microbeam array 20' is interleaved or interlaced with the second heavy ion microbeam array 20" to form a substantially continuous three dimensional irradiation pattern 24 at the target 22 where the microbeams in the two interleaving arrays touch and slightly overlap to produce a non-segmented radiation field. This produces a solid and nearly uniform pattern 24 of heavy ion radiation only within the target tissue 22.

The interleaving of the arrays 20' and 20" can be achieved by providing two heavy ion sources that propagate spaced rows of planar heavy ion microbeams from two orthogonal directions, wherein the second array 20" is shifted in the direction perpendicular to the microbeam planes with respect to the first array 20' so that the rows of planar heavy ion microbeams of the second array 20' fall within the spaces between the rows of planar heavy ion microbeams of the second array 20".

Alternatively, a first array 20' of spaced rows of planar heavy ion microbeams can be directed from a single source of heavy ions in a first direction, and the source can be subsequently moved to a new location, or the subject itself, including the target 22 can be rotated to produce a second exposure, this time for the array 20" of spaced rows of planar heavy ion microbeams directed to the target in a second direction. Again, the second array 20" is shifted in a direction perpendicular to the plane of the microbeams 20 with respect to the first array 20' so that the rows of planar heavy ion microbeams of the first array 20" fall within the spaces between the rows of planar heavy ion microbeams of the second array 20'. This can also be achieved by moving the source or the target in a direction perpendicular to the plane of the microbeams 20 between dosages delivered from the first and second arrays 20' and 20".

In both cases, the two arrays 20' and 20" can be directed into the target 22 from two orthogonal directions by either rotating the subject or moving the source around the subject. The axis of rotation is generally positioned through the center of the target volume 22, and perpendicular to the microbeam planes. In this way, the beams 20 of the first array 20' in the first irradiation direction remain substantially parallel to the beams 20 of the second array 20" after rotation.

Substituting heavy ions, such as He, Li, Be, B, C, N, O, F, Ne, Na, Mg, etc, for x-rays in the manner according to the present invention yields a rate of beam broadening suitable for a specific depth of the target in the tissue. This is because for the same depth of the tissue the beam broadening decreases as the atomic number and the mass of the heavy ion increase. At the same time, to have the benefit of the tissue-sparing effect of heavy ions the thickness of the heavy ion proximal to the target should stay below 0.8 mm.

The use of these possible heavy ions in interlaced heavy ion microbeams produces significant benefits never before achieved in the prior art. In particular, this embodiment of the present invention provides a combination of the advantages of interlaced x-ray microbeam technology described above with the advantages of heavy-ion therapy. Furthermore, the method has several technical advantages over interlaced x-ray microbeams.

First, the interlaced x-ray microbeam method is limited in its applicability to small and medium size tumors only because the relatively small spacing between the x-ray beams leads to the production in the surrounding normal tissues a substantial amount of x-ray scattering and, thus, a larger radiation leakage between the beams, known as "valley dose." This problem essentially does not exist with heavy ion beams as they do not undergo wide angle scattering, and the dose produced by particle fragmentation is very small. Therefore, interlaced heavy ion microbeams can be applied also to larger tumors.

The criterion for evaluating the adequacy of the method to be used in a certain application is that the beam's broadening in the healthy tissue proximal to the target should not lead to a beam thickness larger than 0.8 mm, which is tentatively called the limit of microbeams' thickness that still retains its sparing effect in normal tissues. Therefore, the spacing of the heavy ion microbeams should be adjusted for each case, depending on the depth of the target volume within a subject, to satisfy this criterion.

Thus, beams of heavy ions of carbon can be used for most applications in the brain, spinal cord, spinal column, the head and neck, and the extremities so long as the thickness of the microbeams at the proximal side of the target volume can be kept below 0.7-0.8 mm. The method can also be applies to the target is the chest or the abdomen is the target can be immobilized.

For treating larger or more deeply seated tumors, one can use heavier ions, such as nitrogen, oxygen, fluorine, neon, sodium, and magnesium. These heavier ions exhibit less beam broadening for the same tissue depth as lighter ions. Therefore, for deeper tumors, microbeams of heavier ions should be used to maintain the same desired maximum beam thickness of 0.8 mm at the proximal side of the target volume.

Second, as shown in FIG. 2, the spacing d between adjacent incident planar heavy ion microbeams 20 can be chosen to be larger than the incident beam thickness t, due to the inherent beam broadening characteristics of heavy ions. Specifically, each individual beam 20 will have a thickness t upon entering the subject 22. Due to the beam broadening characteristics of heavy ions, this thickness will increase as the beam travels through the subject until it reaches a beam thickness T as it enters the target volume 24. The beam thickness T at the proximal side of the target volume is greater than the thickness t of the beam as it enters the subject. Thus, after determining the depth of the target volume 24 within the subject 22, one can calculate what the thickness T of the beam 20 will be as it reaches the target volume 24 based on the incident beam thickness t and the type of heavy ions used. Once the target volume beam thickness T is calculated, the center to center (i.e., on-center) planar beam spacing D can be chosen so that adjacent beams from the two interlacing directions, which are preferably orthogonal to each other, just touch as they enter the target volume 24, or preferably slightly overlap at the proximal side of the target. This center to center planar beam spacing D will generally be slightly smaller than twice the beam thickness T at the entrance to the target volume. For that to happen, as a result of the inherent beam broadening characteristics of heavy ions, the distance d between adjacent beams 20 as the beams enter the subject 22 can be made greater than the thickness t of the beams as measured at the same proximal point of the subject.

The beam's thickness at the entrance to the target volume should not be larger that 0.8 mm because experimental results show that microbeams' sparing effect in normal tissues is compromised for thicker beams. This beam thickness can be calculated in a given subject using Monte Carlo simulations.

In contrast, planar x-ray beams do not broaden and will, therefore, require a spacing (d) between adjacent microbeams slightly smaller than the incident beam thickness (t) to ensure that there will be no irradiation gaps in the target volume. The heavy ion beams' broadening traits will allow a planar beam spacing D (on-center) in the incident beam array that is wider that twice the beam's thickness t. As the two beam arrays 20, 20a penetrate the tissue 22 and approach the target 24, their natural broadening makes up for the extra beam spacing and will result in adjacent beams from the two interlacing arrays touching each other and even slightly overlapping at the entrance to the target. The benefit is an unsegmented radiation field at the target 24 while using fewer microbeams. Because of the larger beam spacing D, the sparing effect of the microbeams in the normal tissue 22 proximal to the target 24 is in fact improved.

Figure 3:
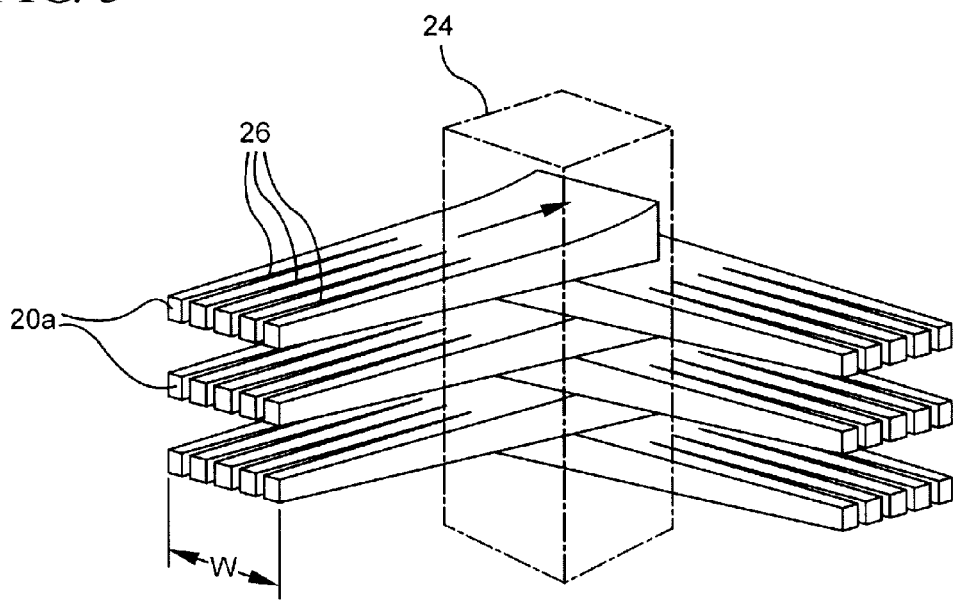
FIG. 3 is a perspective view of two interlacing arrays of additionally segmented planar heavy ion microbeams according to the present invention.

Third, because beams of heavy ions broaden in all directions, the planar beams can also be laterally segmented to form a laterally segmented beam 20a, as shown in FIG. 3. Specifically, the microbeams (i.e., microplanar beams) in each of the two interlacing arrays 20a can be additionally segmented along their lateral width dimension W, leaving gaps 26 regularly spaced in a direction parallel with the plane of the beam. As the beams 20a approach the target 24, the natural broadening of the beams will close those gaps 26, thus allowing the target to receive an unsegmented radiation field. This additional second beam segmentation will also improve the sparing effect in the normal tissue 22 proximal to the target 24.

Finally, because the position of the Bragg peak of the heavy ions (i.e., the depth within the target volume at which the heavy ions lose all their energy) can be pre-determined through calculation using empirical data, the energy of the heavy ions can be pre-selected such that the ions will stop traveling at a known depth within the target. Furthermore, successive irradiations of heavy ions having varying energy and intensity can be directed from a single location to deliver a uniform dose through the depth of the target volume. This technique, known as Bragg-peak spreading is shown in FIG. 4.

Figure 4:
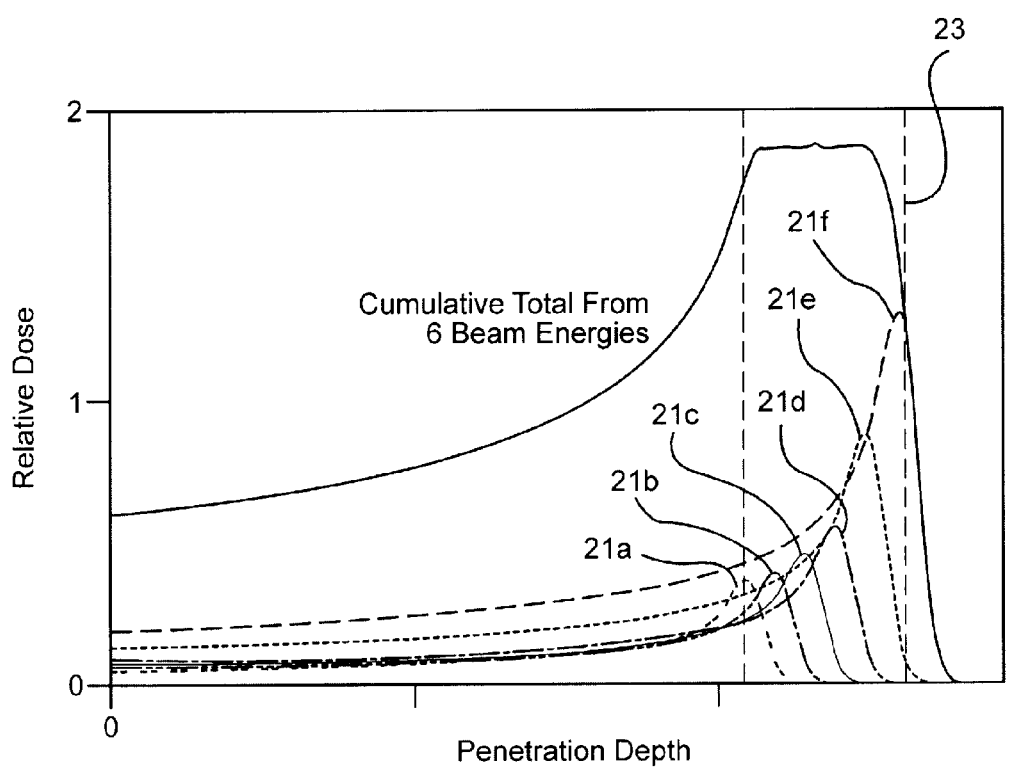
FIG. 4 is a graph illustrating a Bragg-peak spreading technique.

Thus, FIG. 4 shows how successive microbeams 21a, 21b, 21c, 21d, 21e, 21f of heavy ions having varied energy and intensity can be selected to deliver a substantially uniform dose of energy within the target volume. This can be achieved by simply adjusting the source of heavy ions to vary the energy and intensity of the heavy ions.

Another method for adjusting the energy and intensity level of a microbeam of heavy ions is to successively interpose a series of plastic filters of varying thickness in the path of a heavy ion microbeam having a known energy. As the microbeam passes through the filters, the energy of the heavy ions is reduced. By successively interposing plastic filters of increasing thickness, the energy of the emerging microbeams can be stepwise reduced, which will result in an energy distribution as shown in FIG. 4.

As also shown in FIG. 4, the maximum energy of the heavy ion microbeams can be selected to ensure that little to no energy is released outside of the target volume. More particularly, the maximum beam energy of the heavy ions can be chosen so that the beam stops at the distal side 23 of the target volume. In this way, the target exit dosage is virtually eliminated.

Figure 5:
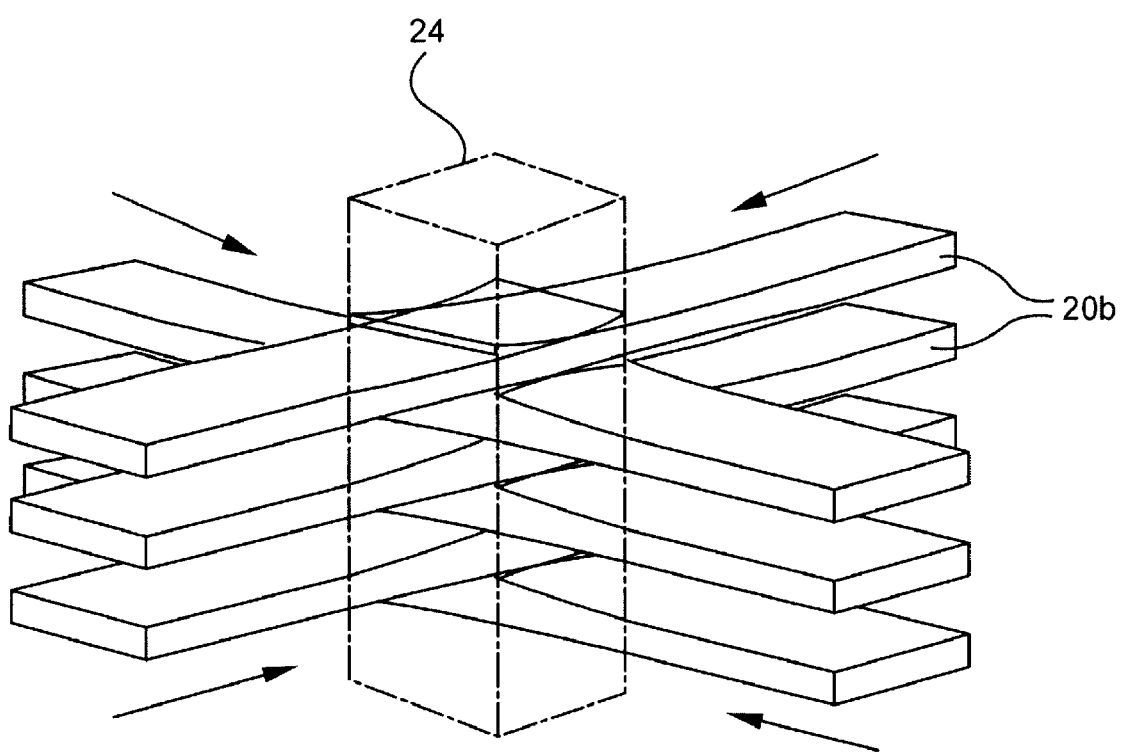
FIG. 5 is a perspective view of four interlacing arrays of planar heavy ion microbeams aimed at a target from ninety degree angles, (i.e., two sets of interlacing arrays aimed at the target from opposite directions), according to the present invention.

As a result, arrays 20b can be aimed at the target 24 from two direct opposite directions, as shown in FIG. 5. Opposite-direction irradiations are not permitted with x-ray microbeams because the array from one direction will reach the distal side of the target, increasing the valley dose produced by the second array in healthy tissue on that side of the target either by producing additional x-ray scattering to increase the valley dose there, or through mechanical beam misalignment, which is amplified at far distances. Irradiations of the target with heavy ion microbeam arrays from opposite directions will not lead to any of these problems and will allow for the reduction to half the incident dose of each array, thus improving the sparing effect of normal tissues by a factor of two.

Figure 6:
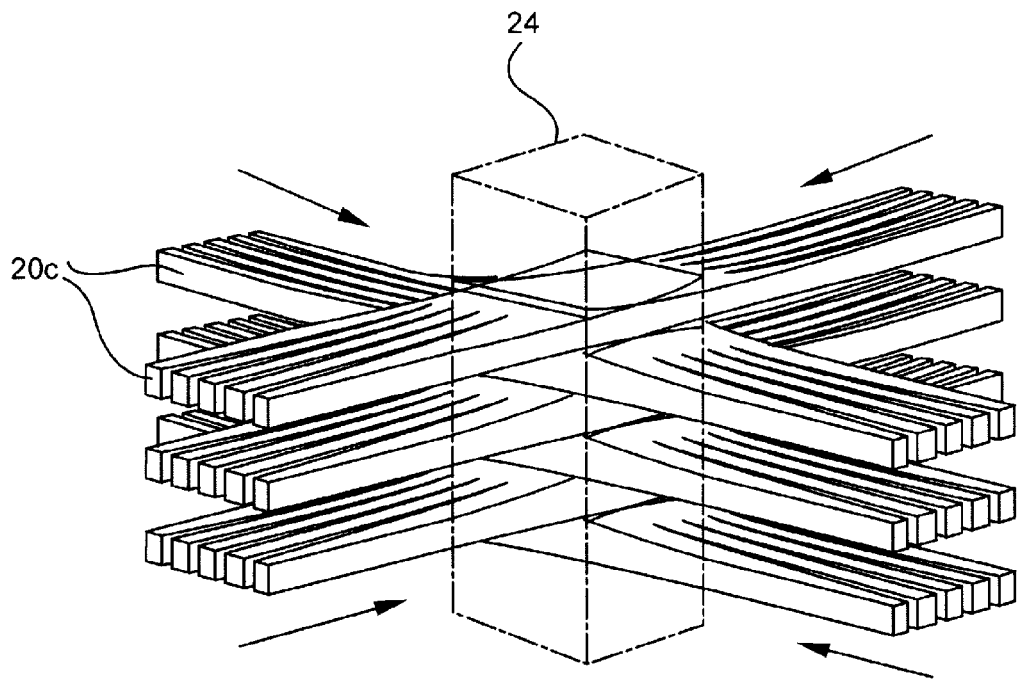
FIG. 6 is a perspective view of four interlacing arrays of additionally segmented planar heavy ion microbeams aimed at the target from ninety degree angles, (i.e., two sets of interlacing arrays at the target from opposite directions), according to the present invention.
Figure 7:
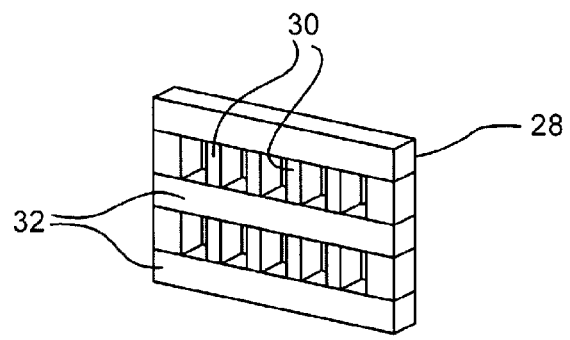
FIG. 7 is a perspective view of a collimator for use with the interlacing arrays of additionally segmented heavy ion microbeams of the present invention.

Laterally segmented planar beams 20c can also directed from direct opposite directions, as shown in FIG. 6. Such arrays of heavy ion microbeams 20, 20a, 20b and 20c can be produced from a broad unsegmented, parallel microbeam by a collimator 28, as shown in FIG. 7. The collimator 28 can be made of tungsten, tantalum, or any other heavy metal. The beams 20a and 20c can be further laterally segmented by adding vertical dividers 30 between the horizontal dividers 32 of the collimator 28, as shown in FIG. 7. If the incident beam is not horizontal, the geometry will be corrected accordingly.

Another type of collimator, called an array aperture collimator, can be used to tailor the shape of the microbeam array to match the cross section of the target volume as viewed from the irradiation direction. For example, the cross-sectional outline of a tumor as viewed from a particular direction can be reproduced on such a collimator or aperture so that an array of microbeams passing through the collimator will have the same outline as the tumor and the safety margin of target irradiation around it. When irradiating the tumor from the selected direction, this will further ensure that non-targeted tissue will be spared.

The source for producing the microbeams of heavy ions according to the present invention can be any conventional heavy ion source. A source providing carbon-12 beams at up to 250 MeV/nucleon, for example, adequate for radiation therapy of most clinically relevant subjects, is an ideal source of heavy ions for use in the present invention. In a preferred embodiment, interlaced heavy-ion microbeams can be clinically implemented using a dedicated heavy ion facility, especially designed to produce a highly parallel beam, i.e., to have a relatively small virtual out-of-plane source size.

A fixed horizontal beam-line with a patient positioned on a chair capable of rotating around its vertical axis will be the most common method of implementing the method. The chair will then be rotated at 90-degree steps to administer the irradiations to the patient from four 90-degree angles. Another method according to the present invention will involve two fixed horizontal beam lines aiming at the target from 90-degree angles. This will allow simultaneous administration of each of the two pairs of the interlacing arrays, thus minimizing any possibility of patient movement during the irradiations. However, the pair of interlacing arrays can also be administered individually. Gantries can be used with this method if they can allow a very low-emittance beam, i.e., highly parallel beams. A gantry rotating around a horizontal axis can be used with a patient lying on a horizontal couch. The gantry will then rotate around the patient at 90-degree angular steps to produce the four 90-degree exposures. Between these exposures the patient's couch is shifted along the axis of the gantry's rotation by half the value of the beam-spacing on-center. Of course the method requires the use of a patient chair or a patient couch with full degrees of translational and rotational positioning capabilities. Image guided methods should be employed to assure adequate targeting.

In yet another method of irradiation, two fixed, mutually orthogonal, inclined beam lines are used. These beam lines can be inclined, for example 45-degrees, to the horizon, producing heavy ion microbeams with their planes perpendicular to an axis which is perpendicular to the axes of the two beam lines. The two beam arrays both aim at the target volume simultaneously or individually, and the subject is positioned on a couch capable of rotating around an axis perpendicular to both beam lines. The beams from the two beam lines will be used to simultaneously or individually expose the subject from two orthogonal directions, with one array being shifted in the direction of the couch's axis of rotation by half the value of the beam spacing on-center with respect to the other. After each such double-exposure, the couch is rotated by 180 degrees around the couch's axis, positioned in the center of the target volume, and the double-exposure procedure is repeated.

EXAMPLE 1

An experiment of the present invention to evaluate the tolerance of the normal rat brain to exposure with iron microbeams of 600 MeV/nucleon was carried out. Rats were irradiated in their brains anteroposteriorly with four horizontal microbeams, each 0.3 mm high, 12 mm wide, spaced 3.5 mm on center, at 2, 10, and 20 Gy. H&E histology 3 months later showed no damage to any brain.

EXAMPLE 2

In another experiment to evaluate the effectiveness of interlaced carbon microbeams, the method according to the present invention was used to ablate a 6.5-mm diameter target in a rabbit's brain. The beam arrays were made of 0.3 mm thick carbon microbeams spaced 10.5 mm on-center. The rabbit was irradiated from four 90-degrees angles with a dose to the target volume of about 40 Gy physical dose in a single session. Assuming an RBE of 2.2, this dose is equivalent to an x-ray dose of 88 GyE. The dose ablated the target volume but there was little or no damage to the surrounding normal brain as evaluated 6 months later by histological studies using H&E tissue staining.

The advantages of heavy ion interlaced microbeams over conventional radiation therapy and radiosurgery are numerous. Interlacing beams of heavy ions exposes the normal tissues to microbeams only, while the target, which can be a tumor, is subjected to a solid, unsegmented radiation field resulting from the interlacing or interleaving of the two beam arrays. The method can ablate hypoxic and other radioresistant tumors because of the heavy ions' high relative biological effectiveness (RBE). The RBE of carbon beams in the energy ranges used for clinical radiation therapy is about 3.0, as compared to 1.0 for x-rays and about 1.1 for protons. The method also produces very sharp dose falloff at the tumor's edge, with 80% to 20% dose falloff of less than a millimeter. Although this dose falloff is not as sharp as that in x-ray interlaced microbeams produced by a synchrotron source, for which the 80% to 20% dose falloff can be less than 0.1 mm, it is still much sharper than that produced by conventional radiation therapy and radiosurgery using high energy x rays or gamma rays, which can be 3-5 mm, and that from proton therapy, which can be 2-3 mm.

There are also numerous advantages of heavy-ion interlaced microbeams over x-ray interlaced microbeams. Use of interlaced heavy ion microbeams essentially has no "valley dose" (i.e., dose between microbeams) because there is no scattering. In this regard, the amount of nuclear fragmentation is small and does not produce a valley dose. The lack of valley dose allows treating large and deeply seated tumors, which cannot be treated with interlaced x-ray microbeams.

Moreover, the method of the present invention can be administered from four directions instead of two because there is no target exit dose. This dilutes the entrance dose by two fold. Also, each microplanar beam can be laterally split into rectangular or square microbeams, thereby further increasing the sparing effect.

Calculating the ratio between the tissue entrance dose (i.e., the skin dose) and the target dose with 4-direction interlaced heavy ion microbeams without lateral beam segmentation yields the following. First, because of its Bragg-peak feature, the dose to the tumor from each exposure is about four times higher than the entrance tissue, i.e., the skin (the exact number depends on the target's depth and size). Second, the divergence of the heavy ion beams makes the microbeams narrower at the entrance to the skin than at the target. This makes the heavy ion microbeam dose at the entrance to the skin about twice as large than that in the target because the dose is defined as the energy deposition in tissue per unit mass of the tissue and if the same beam energy passes through a volume twice smaller the dose will be twice larger. Third, because in each pair of interlacing microbeams the doses are not adding to each other, in a 4-direction interlacing the tumor receives only twice more dose compared to a single exposure and not four times. Therefore, in overall when using interlaced heavy ion microbeams from four directions with no lateral microbeam splitting, the physical dose to the skin in each microbeam is about a ¼th of the dose to the target. Finally, the comparisons with the entrance dose from conventional radiation therapy cannot be made without the detailed knowledge of the conventional radiation therapy's skin sparing effect.

Applying similar calculations as above to evaluate the ratio of the skin dose to the tumor dose in conventional radiation therapy and radiosurgery with high energy x-rays and gamma rays is not possible because of the skin-sparing effect of the conventional radiations used. All that can be said is that after the range of the skin sparing effect, which can be about 1 cm, the conventional radiation in attenuated with distance as opposed to heavy ion beams in which the Bragg-peak feature boosts the dose to the target.

Although carbon beams can be used for treating most tumors of the brain, spinal cord, spinal column, head and neck, and the extremities while keeping the width of the microbeams at the proximal side of the target below 0.8 mm, for more deeply seated tumors that requirement may not be satisfied with carbon beams because of the excessive beam broadenings it will produce. For those applications ion beams heavier than carbon will be necessary because for beam energies producing the same tissue depth the beam broadening produced by ions heavier than carbon is smaller than that of carbon. Possible beams for these applications are N, O, F, Ne, Na, and Mg.

As a result, the present invention provides a method of administering interlaced microbeams of heavy ions to a target with very little or no valley dose in the microbeam arrays delivered to surrounding normal tissue. In addition, the microbeam dose in skin is about the same as the tumor dose and the dose falloff at the tumor's edge is very sharp. Thus, hypoxic and other radioresistant tumors can be treated much easier by overcoming their radioresistance. These properties of the heavy ion microbeams make them ideal for treating a wide range of benign as well as malignant and highly malignant tumors, mostly of the brain, spinal cord, spinal column, head and neck, and the extremities. The method can also be ideal for treating pediatric brain tumors and metastatic tumors of the brain, spinal cord and the spinal column. However, tumors of the chest and the abdomen cannot be treated with the method because of the breathing and cardiac movements of theses organs, and can be treated by this method only if the breathing and the heart beat can be stopped for 10-20 minutes using lowered body temperatures.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for delivering therapeutic heavy ion radiation to a subject comprising the step of delivering a therapeutic dose of heavy ions substantially only to a target volume within the subject by generating a broad field of radiation effect substantially only within the target volume, the broad field of radiation effect not being generated in non-targeted tissue of the subject, said delivering comprising irradiating the target volume with at least two arrays of heavy ion microbeams, the at least two arrays each having at least two parallel, spatially distinct heavy ion microbeams, and wherein the step of delivering the microbeams further includes the step of interleaving the at least two arrays substantially only within the target volume to form a substantially continuous broad beam of radiation substantially only within the target volume,
 wherein the arrays of heavy ion microbeams comprise parallel beam planes and a substantially constant spacing between adjacent beam planes, and wherein said step of interleaving the at least two arrays comprises the steps of:
  irradiating the target volume in a first direction with a first one of the at least two arrays of heavy ion microbeams;
  angularly displacing a second one of the at least two arrays from the first one of the at least two arrays by rotating one of the subject and a source generating the at least two arrays about an axis positioned through a center of the target volume, the axis being perpendicular to the parallel beam planes;
  translating the second one of the at least two arrays in a direction perpendicular to the parallel beam planes by a distance substantially equal to half the spacing between adjacent beam planes on-center; and
  irradiating the target tissue in a second irradiation direction with the second of the at least two arrays, and
 wherein each of the parallel, spatially distinct heavy ion microbeams comprises a first beam thickness upon entering the subject and a second beam thickness upon entering the target volume, the second beam thickness being greater than the first beam thickness, and wherein the method further comprises the step of spacing adjacent beams of each array such that the distance between adjacent beams is greater than the first beam thickness.

2. The method as defined in claim 1, wherein the at least two arrays are angularly displaced in ninety degree increments so that the radiation is administered from four orthogonal directions.

3. The method as defined in claim 1, wherein the steps of irradiating the target volume in the first and second direction comprises the step of delivering heavy ions at a predetermined energy such that the heavy ions will stop traveling at a known depth within the target volume.

4. The method as defined in claim 3, wherein the at least two arrays deliver heavy ions simultaneously to said target volume.

5. The method as defined in claim 1, wherein the heavy ions are selected from the group consisting of heavy ions of He, Li, Be, B, C, N, O, F, Ne, Na, and Mg.

6. The method as defined in claim 1, further comprising the step of shaping the cross-sections of each of the at least two microbeam arrays to match the cross-sectional shape of the target volume in the first and second irradiation directions.

7. The method as defined in claim 1, further comprising the step of selecting the heavy ions depending on the depth of the target volume within the subject so that the thickness of the beams entering the target volume is less than 0.8 mm.

8. The method as defined in claim 1, wherein the step of delivering the microbeams further comprises the step of spreading the Bragg-peak of the heavy ions among the microbeams to produce a uniform dose distribution throughout the target volume.

9. The method as defined in claim 8, wherein said step of spreading the Bragg-peak of the heavy ions in each microbeam comprises the step of stepwise adjusting the energy and intensity of the heavy ions in each microbeam.

10. The method as defined in claim 8, wherein said step of spreading the Bragg-peak of the heavy ions in each microbeam comprises the step of successively interposing plastic filters of varying thickness in the path of a microbeam.

11. The method as defined in claim 8, wherein the step of spreading the Bragg-peak of the heavy ions in each microbeam comprises the step of correcting the Bragg-peak spreading routine based on the relative biological effectiveness (RBE) of the ions so that the x-ray-photon-equivalent dose is uniform in the target and not the physical dose.

12. The method as defined in claim 1, wherein two arrays of microbeams are delivered from two orthogonal, fixed, horizontal beam lines producing horizontal heavy ion microbeams, both beam lines aiming at the target volume with a subject positioned on a chair capable of rotating around a vertical axis, the beams from the two beam lines simultaneously exposing the subject from two orthogonal directions, with one array being shifted vertically by half the value of the beam spacing on-center with respect to the other array, and wherein the chair is rotated by 180 degrees along an axis passing through the center of the target and the beams from the two beam lines simultaneously expose the subject from two orthogonal directions in a second exposure.

13. A method for delivering therapeutic heavy ion radiation to a subject comprising the step of delivering a therapeutic dose of heavy ions substantially only to a target volume within the subject by generating a broad field of radiation effect substantially only within the target volume, the broad field of radiation effect not being generated in non-targeted tissue of the subject, said delivering comprising irradiating the target volume with at least two arrays of heavy ion microbeams, the at least two arrays each having at least two parallel, spatially distinct heavy ion microbeams, and wherein the step of delivering the microbeams further includes the step of interleaving the at least two arrays substantially only within the target volume to form a substantially continuous broad beam of radiation substantially only within the target volume,
 wherein the arrays of heavy ion microbeams comprise parallel beam planes and a substantially constant spacing between adjacent beam planes, and wherein said step of interleaving the at least two arrays comprises the steps of:
  irradiating the target volume in a first direction with a first one of the at least two arrays of heavy ion microbeams;
  angularly displacing a second one of the at least two arrays from the first one of the at least two arrays by rotating one of the subject and a source generating the at least two arrays about an axis positioned through a center of the target volume, the axis being perpendicular to the parallel beam planes;

translating the second one of the at least two arrays in a direction perpendicular to the parallel beam planes by a distance substantially equal to half the spacing between adjacent beam planes on-center;

irradiating the target tissue in a second irradiation direction with the second of the at least two arrays; and laterally segmenting the heavy ion microbeams along their beam width thereby leaving gaps regularly spaced in a direction parallel with the plane of the beam at a point where the beam enters the subject, wherein heavy ions are not present in said gaps and said gaps diminish in width and eventually disappear upon entering the target volume due to broadening of the heavy ion beam.

14. The method as defined in claim 13, wherein said microbeams are laterally segmented by a collimator made of a heavy metal.

15. A method for delivering therapeutic heavy ion radiation to a subject comprising the step of delivering a therapeutic dose of heavy ions substantially only to a target volume within the subject by generating a broad field of radiation effect substantially only within the target volume, the broad field of radiation effect not being generated in non-targeted tissue of the subject, said delivering comprising irradiating the target volume with at least two arrays of heavy ion microbeams, the at least two arrays each having at least two parallel, spatially distinct heavy ion microbeams, and wherein the step of delivering the microbeams further includes the step of interleaving the at least two arrays substantially only within the target volume to form a substantially continuous broad beam of radiation substantially only within the target volume, wherein the arrays of heavy ion microbeams comprise parallel beam planes and a substantially constant spacing between adjacent beam planes, and wherein said step of interleaving the at least two arrays comprises the steps of:

irradiating the target volume in a first direction with a first one of the at least two arrays of heavy ion microbeams;

angularly displacing a second one of the at least two arrays from the first one of the at least two arrays by rotating one of the subject and a source generating the at least two arrays about an axis positioned through a center of the target volume, the axis being perpendicular to the parallel beam planes;

translating the second one of the at least two arrays in a direction perpendicular to the parallel beam planes by a distance substantially equal to half the spacing between adjacent beam planes on-center; and irradiating the target tissue in a second irradiation direction with the second of the at least two arrays, and wherein said inter-beam spacing of said at least two arrays is selected taking into account the inherent broadening of the heavy ion microbeams so that a path of heavy ions irradiating the target volume from the first direction only intersects a path of heavy ions irridating the target volume from the second direction upon entering the target volume and wherein the thickness of the beams entering the target volume is less than 0.8 mm.

16. A method for delivering therapeutic heavy ion radiation to a target volume within a subject comprising the steps of:

delivering a first array of parallel heavy ion microbeams to the subject from a single fixed beam line, the microbeam array comprising a plurality of parallel microbeams, each microbeam having a first beam thickness upon entering the subject, a second beam thickness upon entering the target volume, a beam width and a beam plane defined by said beam width, the second beam thickness being greater than the first beam thickness due to broadening of the heavy ion beams;

rotating the subject about an axis perpendicular to the beam plane;

translating the subject in a direction perpendicular to the beam plane by a distance substantially equal to half the beam spacing between adjacent beam planes on-center; and delivering a second array of parallel heavy ion microbeams to the subject from the fixed beam line, the second microbeam array comprising a plurality of parallel microbeams, each microbeam having a first beam thickness upon entering the subject and a second beam thickness upon entering the target volume, the second beam thickness being greater than the first beam thickness due to broadening of the heavy ion beams, wherein a first microbeam of the first microbeam array entering the subject is spaced from an adjacent second microbeam of the first microbeam array entering the subject to produce a gap between the first and second microbeams, said gap being greater than the first beam thickness of the microbeams of both the first and the second microbeam arrays, and wherein a first microbeam of the second microbeam array entering the subject is spaced from an adjacent second microbeam of the second microbeam array entering the subject to produce a gap between the first and second microbeams, said gap being greater than the first beam thickness of the microbeams of both the first and the second microbeam arrays.

* * * * *